United States Patent [19]

Miura et al.

[11] Patent Number: 5,132,012

[45] Date of Patent: Jul. 21, 1992

[54] LIQUID CHROMATOGRAPH

[75] Inventors: Junkichi Miura, Hitachi, Japan; Andreas Manz, Basel, Switzerland; Yoshio Watanabe; Yuji Miyahara, both of Hitachi, Japan; Hiroyuki Miyagi, Kokubunji, Japan; Keiji Tsukada, Katsuta, Japan

[73] Assignee: Hitachi, Ltd., Tokyo, Japan

[21] Appl. No.: 369,853

[22] Filed: Jun. 22, 1989

[30] Foreign Application Priority Data

Jun. 24, 1988 [JP] Japan .................. 63-154763
Sep. 9, 1988 [JP] Japan .................. 63-224663

[51] Int. Cl.⁵ .............. B01D 15/08; G01N 30/02
[52] U.S. Cl. .................. 210/198.2; 55/386; 73/61.52; 422/70; 422/82.01; 422/68.1
[58] Field of Search .......... 422/68.1, 70, 82.01, 422/82.03; 210/198.2; 55/386; 73/61.1 C

[56] References Cited

U.S. PATENT DOCUMENTS

| | | | |
|---|---|---|---|
| 3,538,744 | 11/1967 | Karasek | 55/386 |
| 4,702,889 | 10/1987 | Cabrera et al. | 422/103 |
| 4,891,120 | 1/1990 | Sethi et al. | 73/61.1 C |
| 4,908,112 | 3/1990 | Pace | 250/461.2 |
| 4,935,040 | 6/1990 | Goedert | 55/386 |
| 4,948,565 | 8/1990 | Bemis et al. | 422/104 |

FOREIGN PATENT DOCUMENTS 230058 11/1985 Japan .
262659 11/1986 Japan .

OTHER PUBLICATIONS

Angell et al., "Silicon MicroMechanical Devices", Apr. 1983, pp. 50-53.
Manz et al., "Picoliter Cell Volume Potentiometric Detector for Open-Tubar Column LC", pp. 326-330, 1982.
Terry et al., "A Gas Aromatographic Air Analyzer fabricated on a Silicon Wafer", pp. 1880-1886, 1979.

Primary Examiner—Robert J. Warden
Assistant Examiner—Theresa A. Trembley
Attorney, Agent, or Firm—Antonelli, Terry Stout & Kraus

[57] ABSTRACT

A liquid chromatograph comprises an analyzing chip in which a capillary is formed in a substrate and a detector section is disposed downstream of the capillary. The capillary is covered so that an inlet opening end and an outlet opening end of said capillary flow path is opened. A frame member has a sample introduction path, a carrier liquid introduction path and a liquid discharge path. The analyzing chip is movably disposed in the frame member so that the inlet opening end and the outlet opening end of the capillary are selectively in communication with and/or under interruption against said sample introduction path, the carrier liquid introduction path and the liquid discharge path. The liquid chromatograph is very small in size but is easy to handle. Incidentally, there is disclosed also a sample introduction apparatus and method for the chromatograph, and an FET type detector suitable for the chromatograph.

7 Claims, 16 Drawing Sheets

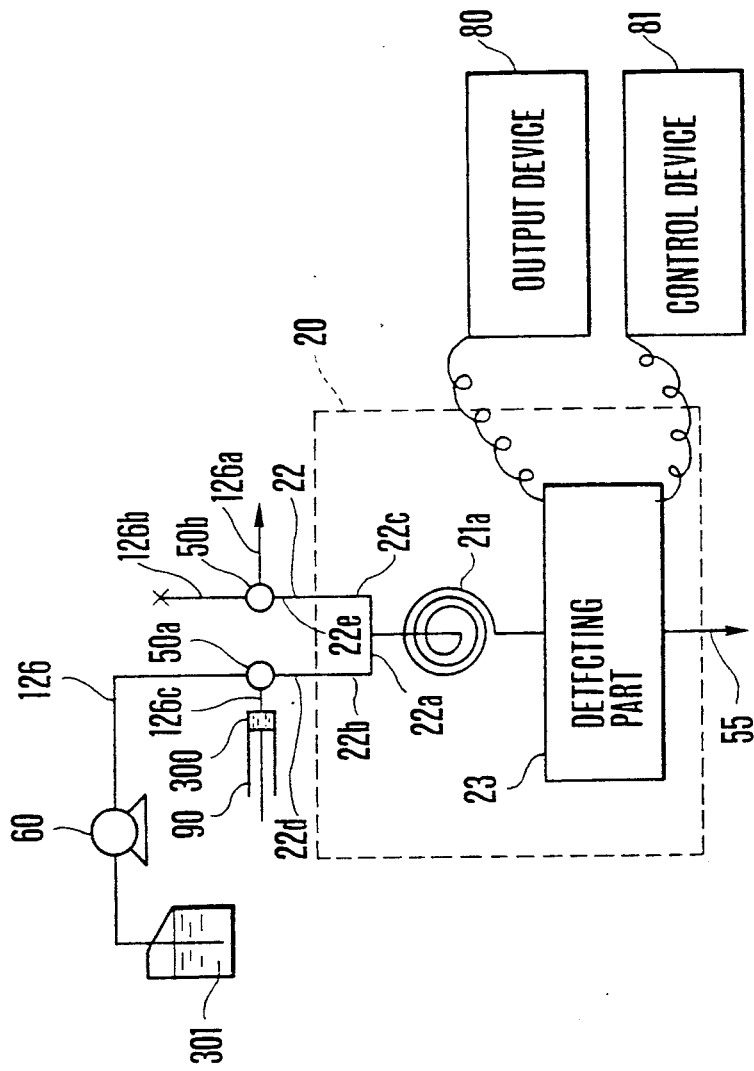

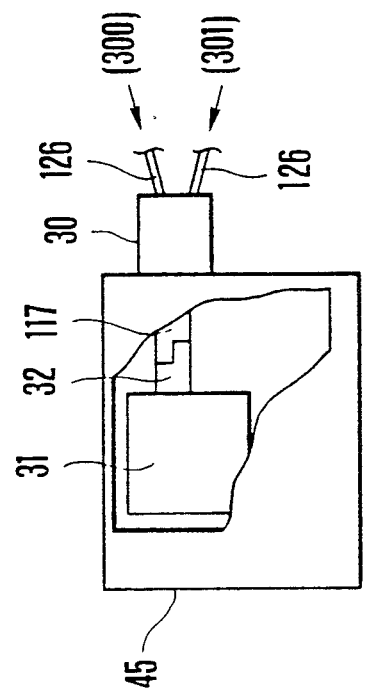

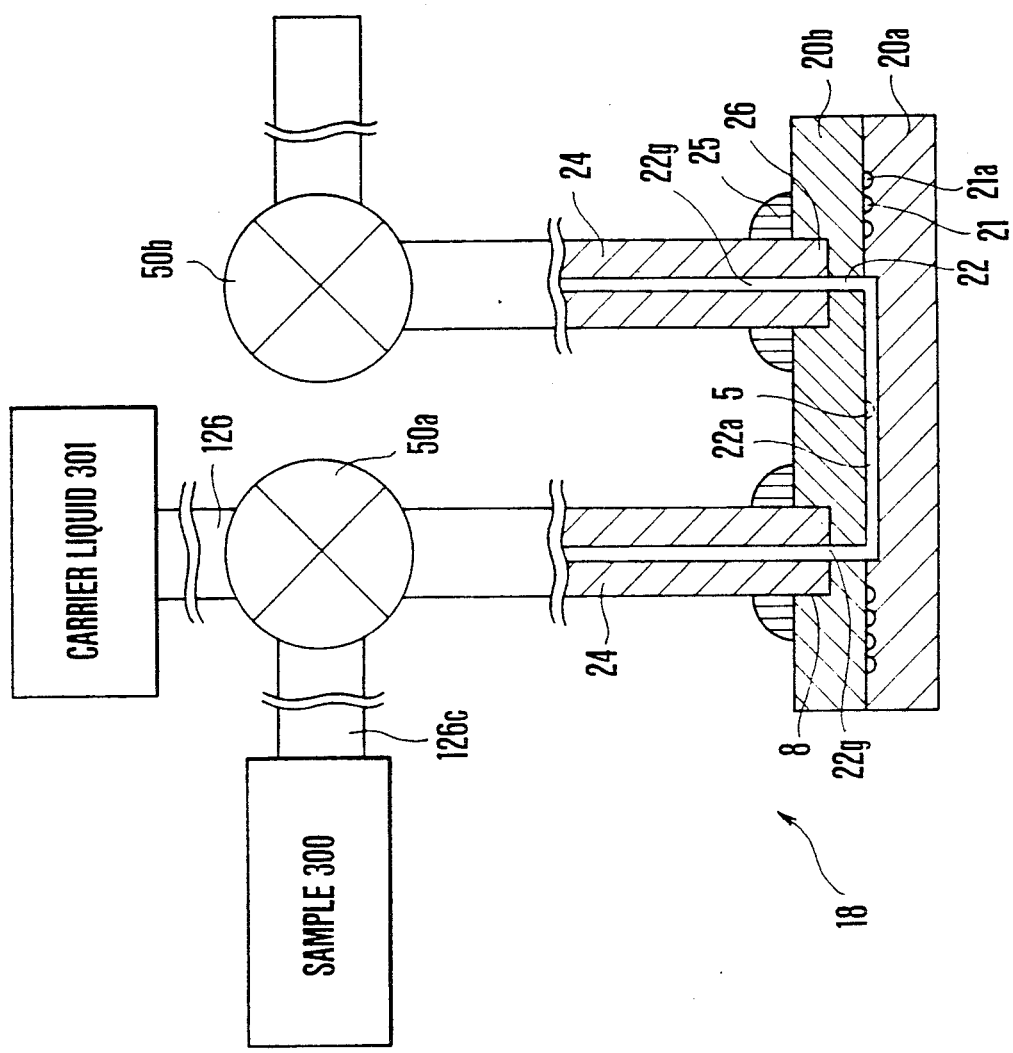

LIQUID CHROMATOGRAPH

BACKGROUND OF THE INVENTION

The present invention relates to a liquid chromatograph, and more particularly to a liquid chromatograph having a miniaturized analytical section for separation and detection of a small amount of sample.

The present invention also relates to a sample introduction apparatus and method suitable for a microliquid chromatograph by using a capillary column as a separation column.

The present invention is also concerned with a detector disposed in a liquid chromatograph for detecting ionic components contained in a liquid sample to be analyzed, and more particularly with a liquid chromatograph detector which is inexpensive and disposable.

In a conventional chromatograph, a carrier liquid delivery section, a sample injection section, a separation column, a detector and the like are provided independently of each other and these sections are connected through conduits. However, with such a structure, it is necessary to solve a variety of technical difficulties in order to miniaturize the analyzer.

For example, since the separation column is composed of a micro bore glass tube having an inner diameter of 0.1 mm or less, the glass tube is fragile and it would be difficult to perform a line connection with other elements and to handle the glass tube.

Also, a dead volume of fittings or connectors would be increased to a level not neglibible in comparison with a capacity of the separation column, so that it would be difficult to enhance a performance, a precision and a reproducibility of the separation and detection of the components contained in the sample.

There has also been provided a conventional apparatus in which a sample injection valve and a detector are directly connected to a separation column in order to reduce a dead volume, for example, in Journal of Chromatographic Science, Vol. 21, July 1983, pp. 326–330, in particular, FIGS. 2 and 3 and the related description. However, even with such an apparatus, it would be difficult to satisfactorily solve the above-described problems.

On the other hand, in a field of gas chromatography, there have been some proposals for miniaturization. For instance, Stephen C. Terry et al., "A Gas Chromatographic Air Analyzer Fabricated on a Silicon Wafer", IEEE, Transactions on Electron Devices, vol. Ed-26, No. 12, December 1979, pp. 1880–1886 shows a gas chromatograph structure in which a capillary column is formed on a silicon substrate and a part of the structure including a detector is integrated. In this publication, there is also a proposal of a method for forming a sample injection valve on the silicon substrate.

Incidentally, Japanese Patent Unexamined Publication No. 61-262659 shows a gas chromatograph in which a thermal conduction detector is disposed on a silicon wafer.

In a liquid chromatograph, in contrast to a gas chromatograph, however, it is necessary to switch over liquid separation flow paths when the sample is introduced into the separation column. It is therefore difficult to miniaturize the analytical section even if the structure of the gas chromatograph proposed in the prior art is applied to the liquid chromatograph without change. Also, the flow path arrangement would be complicated.

More specifically, in case of gas chromatography, the introduction of the sample gas is performed under a pressure (relatively low level) substantially equal to a pressure of the column, whereas, in the case of liquid chromatography, the same method as the gap chromatography can not be used because the pressure in the column should be high. The sample may be injected similarly only when the pressure is 30–40 kgf/cm$^2$. Thus, a sample valve where the sample has been injected beforehand is provided to allow the sample to be introduced into column when the sample valve is operated or switched over. The liquid chromatograph should have a flow switching-over valve having a high mechanical strength or a separation column having a high mechanical strength which is capable of arranging the mechanically strong switching valve.

A first object of the invention is to provide a liquid chromatograph that is easy to handle in spite of high miniaturization of an analyzer provided with a sample components separation ability.

In addition, the prior art method for forming the sample injection valve on the silicon substrate as shown with reference to gas chromatography is superior in view of the resulting small dead volume, but is disadvantageous because of requirements in a complicated structure, complicated manufacture, steps, and means for liquid-tight seal under high pressure required for liquid chromatography.

A second object of the present invention is provide a sample introduction apparatus for a capillary liquid chromatograph which is simple in structure and easy to manufacture, and to provide a method therefor.

Furthermore, according to the conventional technique proposed in the above-mentioned literature by Stephen C. Terry et al., since the thermal conductivity detector which is effective only on a gas sample is used, there is a problem that a liquid sample cannot be analyzed. Moreover, a certain carrier liquid has a high electrical conductivity, and if the liquid sample is brought into direct contact with electrodes of the conventional detector, a noise in an output signal from the detector would be unduly large. Thus, there has been no attempt of applying the conventional electrical conductivity detector to a liquid chromatograph.

In view of the above-described deficiency, the third object of the invention is to provide a liquid chromatograph which is small in size and inexpensive and which is capable of detecting ionic components contained in the liquid sample without fail.

SUMMARY OF THE INVENTION

In order to attain the above-mentioned first object of the invention, there is provided a liquid chromatograph characterized by comprising an analyzing chip in which a capillary flow path or passage is formed in a silicon or borosilicate glass substrate and a detector section is arranged downstream of said capillary flow path, said capillary flow path being covered so that an inlet opening end and an outlet opening end of said capillary flow path are opened, and a frame member having a sample introduction path, a carrier liquid introduction path and a liquid discharge path therein, wherein said analyzing chip is movably disposed in said frame member.

According to the present invention, the analyzing chip having the sample components separating function and detection function is disposed movably within the frame member, whereby the analyzing section per se may also have the function of the switching valve. Also, in connection with the simplification of the structure of the analyzing section, the overall system may be made compact with ease.

According to the present invention, the above-mentioned second object is attained by a sample introduction apparatus and method wherein a sample is filled to a sample introduction flow path communicated with a capillary and having an inner diameter larger than that of the capillary, the sample is pressurized for a predetermined period of time to transfer a part of the sample in the sample introduction flow path into the capillary, then the sample in the sample introduction flow path is replaced by carrier liquid, and thereafter, the carrier liquid is fed from the sample introduction flow path to the capillary.

An inner diameter dc and a length Lc of the capillary and a flow resistance (pressure drop) $\Delta P$ of the capillary are under the following relationship.

$$\Delta P = \frac{4 \cdot \eta \cdot \phi \cdot Lc \cdot F}{\pi \cdot dc^4} \quad (1)$$

where $\eta$ is the viscosity of the liquid, $\phi$ is a coefficient determined the sectional configuration of the capillary and the condition of the inner surface thereof, and F is a flow rate of the liquid.

Accordingly, when an injection pressure is kept at a level much lower than the pressure $\Delta P$ for causing the flow rate that is necessary for analysis, the amount of the sample penetrating into the capillary is negligible, even when the sample introduction flow path is filled with the sample. For this reason, the inner diameter of the sample introduction flow path may, for example, be selected to be ten times or more larger than that of the capillary and the sample is injected into the sample introduction flow path substantially under the atmospheric pressure. The sample is then pressurized for a predetermined period of time while closing one end of the flow path, and it is possible to control the amount of sample injected into the capillary in accordance with a product of pressure and the period of time. The sample within the sample introduction flow path is replaced by the carrier liquid after the injection of the sample into the capillary and the carrier liquid is fed under the pressure determined by the equation (1) while closing one end of the sample introduction flow path. The carrier liquid is introduced into the capillary so that the sample is moved through the capillary.

Furthermore, in order to attain the above-mentioned third object of the invention, there is provided a detector arranged in a liquid chromatograph sample, in which a planar plate is bonded on a surface, for analyzing component ions contained in the liquid, of a substrate of a semiconductor formed with groove portions or a combination of a semiconductor and a dielectric member, a flow path for the liquid sample is defined by the planar surface and the groove portions, and there is provided an FET (field effect transistor) type chemical sensor including a wall surface of a part of the flow path as a gate insulative membrane.

Also, it is preferable that a ion selective membrane be formed on the gate insulative membrane formed on the wall surface of the part of the flow path.

The substrate is made of silicon and borosilicate glass, the gate insulative membrane is formed of $SiO_2$ or by depositing, on $SiO_2$, at least one layer made from a material selected from $Si_3N_4$, $Al_2O_3$, $Ta_2O_5$ and $ZrO_2$, and the substrate contacted with the insulative membrane is provided with source, drain and channel-regions.

Furthermore, the FET and the column for separation of the liquid sample are formed integrally with the substrate.

With such an arrangement, the liquid sample will flow through a flow path defined between the groove portion formed in the substrate and a plane of the planar plate bonded to the substrate. In this case, since the inner wall surface of the groove portion is coated with the insulative membrane, it is possible to protect the substrate from an electrical noise or a chemical contamination. In addition, the insulative membrane is used as a gate insulative membrane of a field effect transistor (hereinafter referred to as FET). A source region and a drain region are formed in the semiconductor substrate contacted with the gate insulative membrane, a voltage is applied between the source and the drain, and a gate voltage is applied through a reference electrode arranged in a suitable position in the flow path to thereby electrically operate the FET. As a result, a change in an electric potential is generated in response to the concentration of a specific ion contained in the liquid sample by the ion selective membrane provided on the gate insulative membrane. Thus, the drain current of the FET is changed in accordance with the concentration of the specific ion. Accordingly, it is possible to detect the concentration of the specific ion in the liquid sample by measuring the drain current.

In a preferred embodiment of the invention, a sample introduction region, a separating column and a detector part are formed on a substrate or base plate made of silicon or glass. A capillary forming the sample introduction region and the separating column is composed of grooves formed by an etching process. The grooves are used to define flow paths in cooperation with a planar plate bonded to the substrate. An analyzing chip composed of the substrate and the planar plate is clamped on both sides by rigid members, preferably formed in disc shapes. An assembly formed integrally of the chip and rigid members may be operated in the same manner as a rotor of a rotary switching valve.

Since the analyzing chip and the rigid member clamping the chip, are arranged in the form of the rotor, it is possible to protect a mechanical fragility of the analyzing chip. The analyzing chip and the rigid members are fixed or integrally formed under the condition that the capillary column groove of the analyzing chip is in communication with grooves of the rigid members. Since the rotor is disposed within the fixed or stationary frame member, the rotor may be in fluid communication with a liquid delivery devices disposed outside through the frame member. With such an arrangement, the line connection with the liquid delivery devices may readily be established.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts through the various views. The drawings are not necessarily to scale, emphasis instead being placed upon illustrating the principles of the invention: in which

FIG. 9 is a schematic view of an overall flow passage of a liquid chromatograph according to an embodiment of the invention;

FIG. 16 is an illustration of an automatic system of the liquid chromatograph to which the invention is applied;

FIG. 17 is a sectional view showing another embodiment of the invention;

DETAILED DESCRIPTION OF THE PREFERRED EMBODIMENTS

Figure 1:
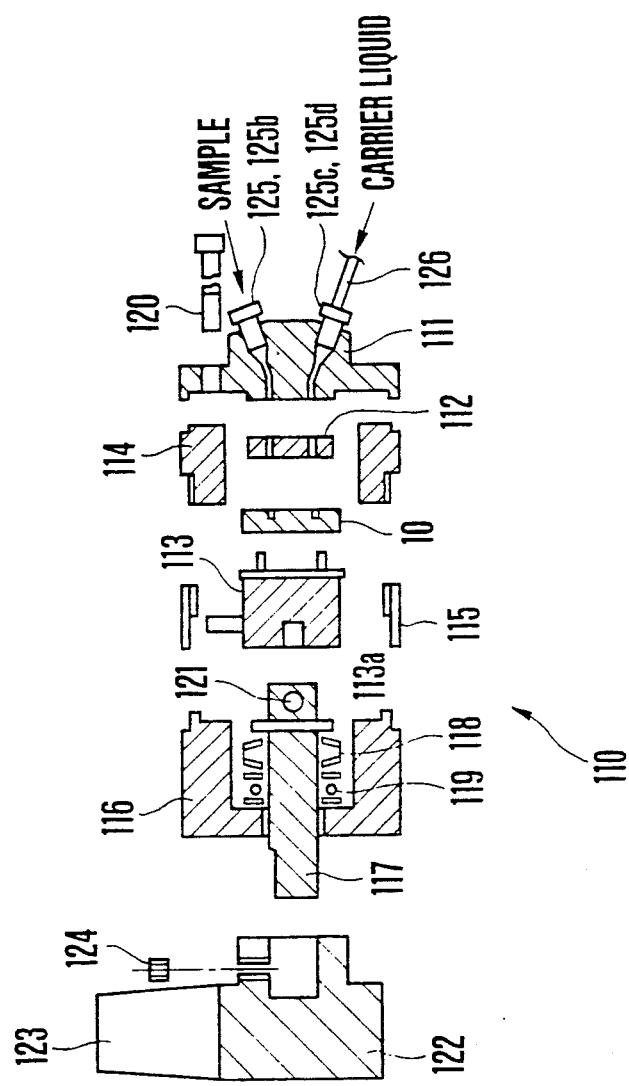
FIG. 1 is a schematic exploded view showing an analyzing section in accordance with one embodiment of the invention.

The present invention will now be described with reference to the accompanying drawings. FIG. 9 shows a concept or principle of the entire flow path or passage of a liquid chromatograph to which the present invention is applied. In FIG. 9, parts 22a, 22b and 22c of a sample introduction section 22 constituted by flow passages 22a, 22b, 22c, 22d and 22e, a capillary column 21a and a detector 23 are formed in a chip 20 including a substrate made of silicon or glass. A switching-over valve 50a for selectively introducing separation carrier liquid or solution 301 and sample 300 is connected to one end, on the flow path 22d side, of the two ends of the U-shaped sample introduction section 22. A switching valve 50b for selective connection to a relief pipe 26a and a blocking or closed pipe 126b is connected to the other end, on the flow path 22e side, of the sample introduction section 22. A control device 81 and an output device 80 such as data processor are connected to a detecting part or detector 23 which serves for detecting separated components or constituents. The sample 300 is injected into the flow path by a syringe or injector 90 through a sample introduction pipe 126c and an excessive part of the sample is discharged from the relief pipe 126a. The carrier solution 301 is fed under pressure by a feed pump 60, and is discharged from a drain 55 after having passed through a tube 126 and the paths or passages within the chip 20.

As described later, a rotor having the chip and a frame member serve as the switching valves 50a and 50b.

One embodiment of the invention will now be described with reference to FIGS. 1 to 8.

Figure 10:
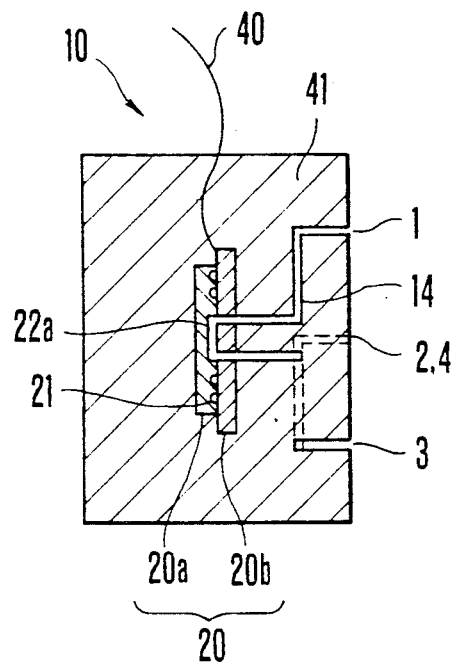
FIG. 10 is an illustration of the rotor in accordance with a second embodiment of the invention.
Figure 11:
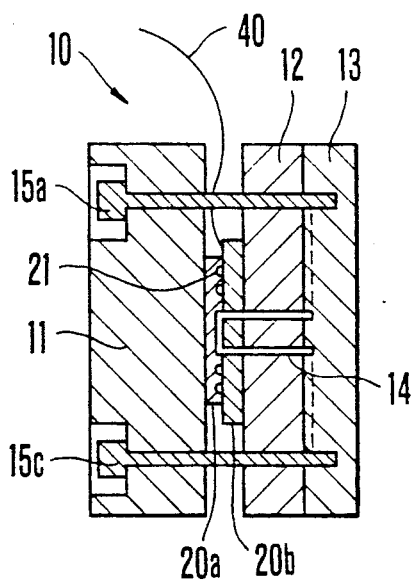
FIG. 11 is a cross-sectional view of a rotor in accordance with a third embodiment of the invention.
Figure 12:
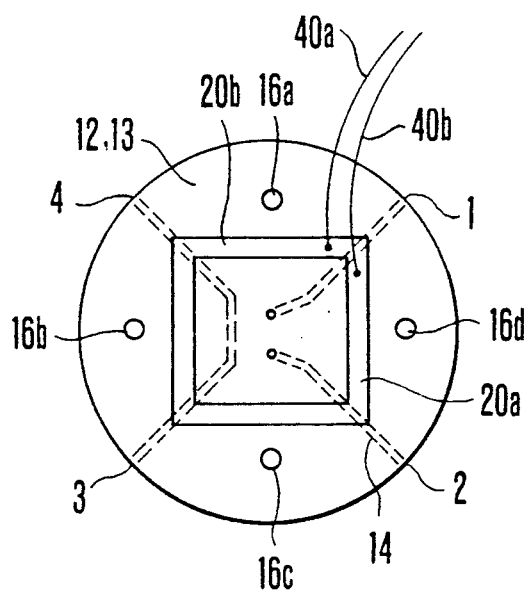
FIG. 12 is a plan view of the rotor shown in FIG. 11.

FIG. 1 is an exploded schematic sectional view showing an analyzer body having a disc-like rotor assembly 10 into which the analyzer chip 20 is integrally incorporated. Details of the rotor 10 will be described later in conjunction with FIGS. 5 and 6; Fig. 10; FIGS. 11 and 12; and FIGS. 13 and 14. A base 111, second body 114, first body 116 and a stator 112 are fixed to each other to form a frame member 110. The rotor 10 and the frame member 110 serve as the switching-over valves 50a and 50b shown in FIG. 9, details of which will be described later with reference to FIGS. 7A-7F. The liquid feed pump 60 (not shown in FIG. 1) is arranged outside of the frame member 110. As described later, the chip and the disc-like rotor assembly 10 made integrally of rigid members so as to surround the chip 20 are interposed between the base 111 and a rotor receiver 13. The first body 116, a fastening adjustment ring 15, the second body 114 and the base 111 are fastened by a fastening screw 120. The stator 112 is securely fixed to the base 111. The rotor 10 is fixed to a shaft 17 through the rotor receiver 113. The rotor 10 is adapted to receive a rotational torque, applied to a head 122 and a head knob 123, through the shaft 117 and the rotor receiver 113 for rotation. A shaft pin 121 is engaged with a recess 113a in the rotor receiver 113 to connect, without slippage, the rotor receiver 113 to the shaft 117. The force to be applied between the disclike rotor assembly 10 and the stator 112 may be adjusted by means of a spring 118, the fastening adjustment ring 115 and the fastening screw 120. A bearing 119 is disposed within the first body 116 so that the rotor receiver 113 may readily rotate. A head mounting screw 124 is used to fasten the head 122 to the shaft 117.

The separation carrier liquid or solution and the sample are introduced into the stator 112 through the pipe 126 and four piping joints 125a to 125d formed in the base 111 to be fed into the disc-like rotor assembly 10. These joints correspond to the Roman numerals I to IV shown in FIGS. 7A-7F. The sample may be injected through the piping joint 125a from the syringe or the like by the manual operation or the automatic operation by means of an automatic sample injection device called "Auto-Sampler".

Figure 2:
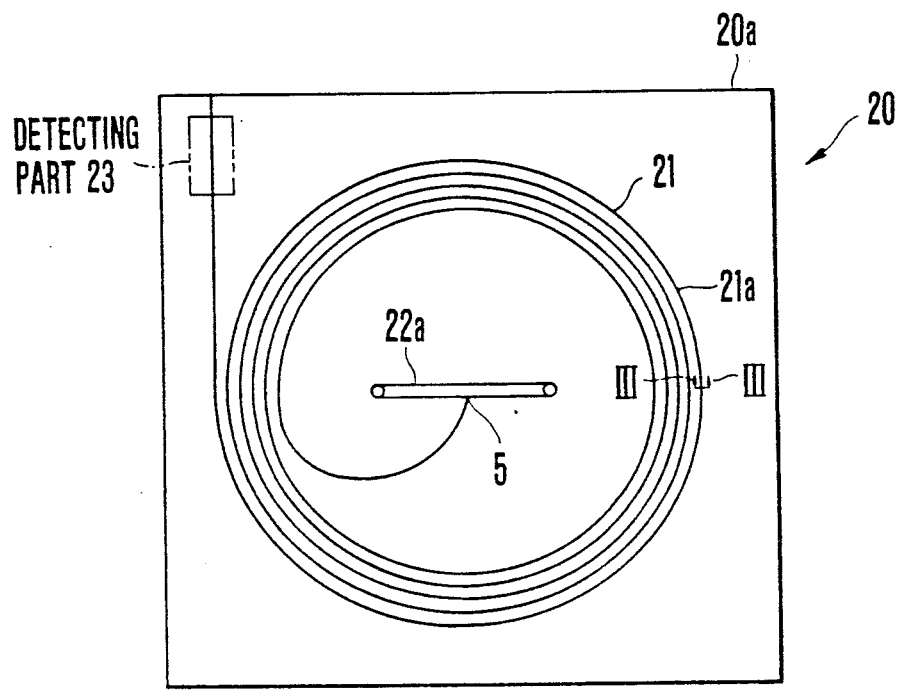
FIG. 2 is a top plan view showing the analytical section chip used in the embodiment shown in FIG. 1.
Figure 3:
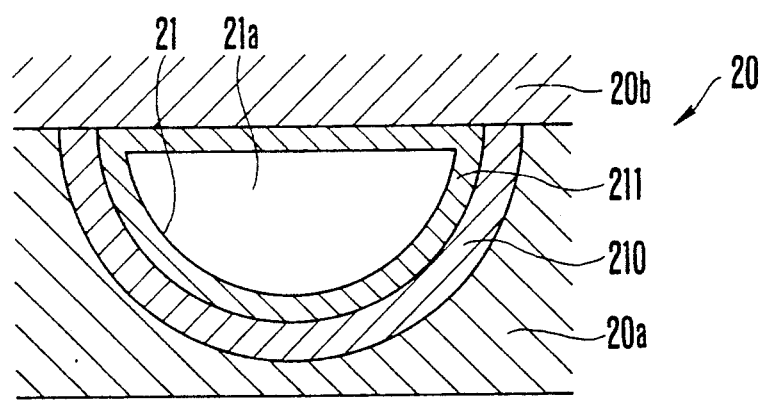
FIG. 3 is a cross-sectional view of the capillary flow path taken along the line III—III of FIG. 2.

FIG. 2 is a plan view showing the analyzer chip 20 incorporated into the disc-like rotor assembly 10 used in the embodiment shown in FIG. 1. FIG. 3 is a sectional view along line III—III of FIG. 2 for illustrating the condition of the capillary 21a defined by the base plate 20a and the planar plate 20b in the analyzer chip 20.

In FIG. 2, a capillary groove 21 is formed in a spiral shape on a surface of the base plate 20a made of silicon or glass. Upstream of the capillary groove 21, there is formed a larger capillary groove serving as a sample receiving region 22a which constitutes a part of the sample introduction section 22. Downstream of the capillary groove 21 and along the capillary groove 21, there is formed a detecting part or detector section 23 such as an electrical conductivity detector and an electrochemical detector. In a preferred form, the detector section may be of a FET type detector to be described later in detail in conjunction with FIGS. 23 to 28. Almost all the region of the capillary groove 21 serves as a separation column for the sample. These grooves are formed through lithography and etching techniques which are used conventionally for production of semiconductor elements. The planar plate 20b which has substantially the same size as that of the base plate 20a is bonded to the surface of the base plate 20a on which the grooves 21 are formed, for forming the flow path or passage 21a.

Typically, an inner diameter of the capillary flow path 21a is 0.5 to 50 micrometers, and preferably 1.5 to 5 micrometers. On the other, an inner diameter of the sample introduction section 22 such as the sample receiving region 22a is typically ten or more times larger than the inner diameter of the capillary groove 21a, and more preferably 50 to 300 times larger than that of the capillary groove 21 (for example, on the order of 1 to 3 mm).

As shown in FIG. 3, after a silicon oxide layer 210 has been formed on the wall of the capillary groove 21 by thermal oxidation prior to the bonding of the planar plate 20b with the base plate 20a, the planar plate 20b made of silicon or glass is fixed to the base plate 20a by an anodic bonding method or the like to form the integral analyzer chip 20. Thereafter, a stationary phase 211 used in a usual liquid chromatograph is formed on an inner surface of the capillary groove 21 through a liquid phase method or a gas phase method.

Figure 4A:
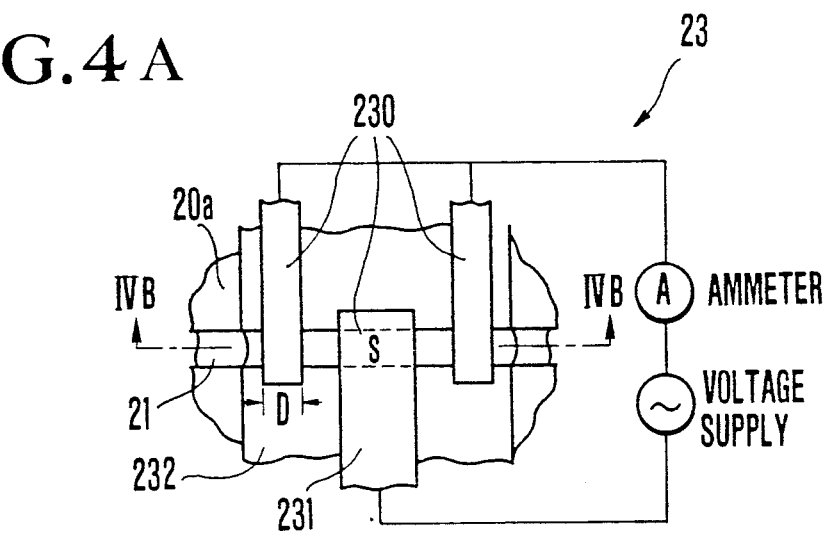
FIG. 4A is a partially broken, fragmentary, enlarged plan view showing the detecting part within the analyzing chip.
Figure 4B:
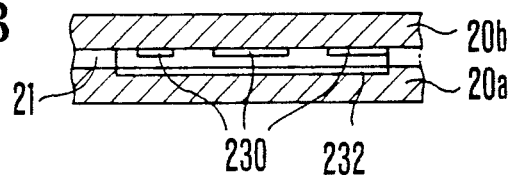
FIG. 4B is a sectional view taken along the line IV-B—IVB of FIG. 4A.

FIGS. 4A and 4B are enlarged views of the detecting part or detector section 23 shown in FIG. 2, FIG. 4A being a partially broken fragmentary view and FIG. 4B being a cross-sectional view taken along the line IVB—IVB of FIG. 4A. These drawings show an example of an electrical conductivity detector. Electrodes 230 are disposed on the downstream side close to the end of the capillary groove 21. The three electrodes 230 shown by way of example are formed on the planar plate 20b. In this example, these electrodes are formed by the lithography after evaporating platinum on the planar plate 20b. Platinum is selected because of its chemical stability and high catalytic function. However, any other material may be used if the material is chemically stable. Since the surface area of the electrodes affects an electric capacitance of the detector section, it is preferable that a width D of each electrode be in the range of 5 to 10 micrometers, and the surface area S of the action electrode 231 be in the range of 100 to 200 square micrometers. In this case, the capacity of the detector 23 will be in the range of 0.5 to 1.2 picoliters. Reference numeral 232 denotes a groove for electrical insulation.

The sample introduced into the capillary groove 21 from the sample introduction section 22 reaches the detector 23 while moving in the capillary groove together with the carrier, i.e., separation solution and being separated into respective constituents or components. At this time, if a high frequency alternating-current voltage is applied between the platinum electrodes 230 appropriately selected for the electrolyte composition in the separation solution, a current will flow in proportion to the concentrations of ions. This current is recorded as a chromatogram, proportional to the concentrations of the ions, on a recorder. When one of the electrodes is used as a reference one, it is possible to use the detector as an electrochemical detector.

Figure 5:
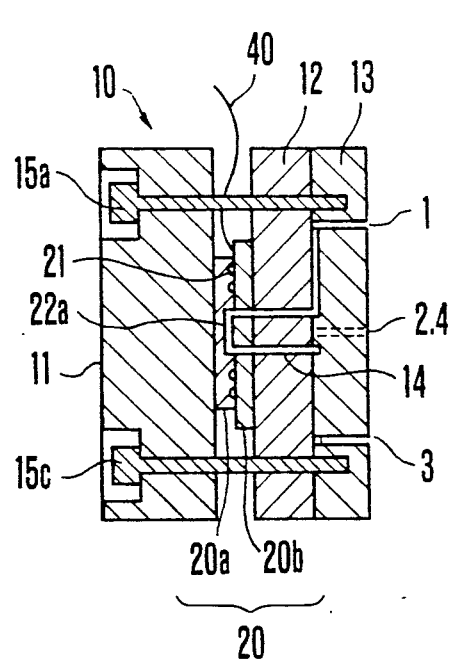
FIG. 5 is a cross-sectional view of a disc-like assembly rotor according to an embodiment of the invention.
Figure 6:
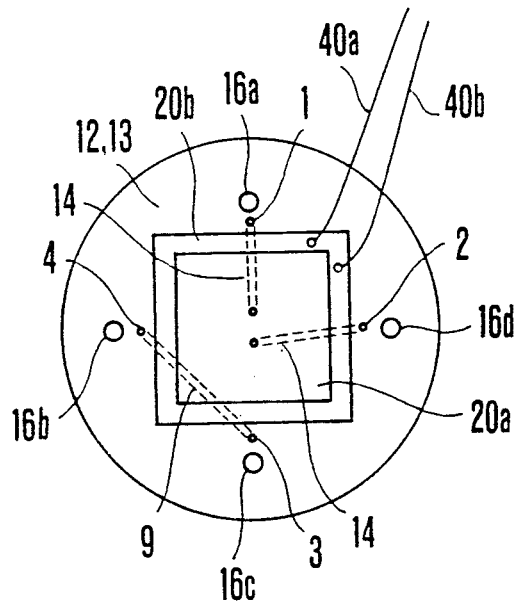
FIG. 6 is a plan view of the rotor shown in FIG. 5.

FIGS. 5 and 6 show a specific example of the disc-like rotor assembly 10 used in the embodiment shown in FIG. 1. FIG. 5 is a cross-sectional view of the rotor, and FIG. 6 is a plan view of the rotor shown in FIG. 5 from which a bottom plate 11 and four screws 15a-15d (15b, 15d not shown) have been removed.

Referring to FIGS. 5 and 6, it is understood that the disc-like rotor assembly 10 comprises the disc-like bottom plate 11 made of rigid material such as stainless steel and ceramics, two upper plates 12 and 13, and the chip 20 composed of the base plate 20a and the planar plate 20b clamped between the bottom plate 11 and the upper plates 12 and 13. A flow path or passage 14 (corresponding to the flow paths 22b to 22e in FIG. 9) for communication with the sample receiving region 22a is formed in the chip 20 and the two upper disc-like plates 12 and 13. An electric power supply lead 40a to the detector 23 provided within the chip 20 and an output lead 40b are connected to the chip 20. Holes 1, 2, 3 and 4 in communication with the pipings through the stator 112 and the base 111 are provided in on the disc-like upper plate 13. Among these holes, the holes 1 and 2 are in communication with the flow path or passage 14 but the holes 3 and 4 are in communication with each other to form a bypass passage 9. The bottom plate 11, the chip 20, and the upper plates 12, 13 are fixed to each other by screws 15a to 15d.

Screw holes 16a to 16d for fastening the bottom plate 11 and the upper plates 12 and 13 are formed in the respective plates corresponding to the screws 15a to 15d. The electric power supply lead 40a and the output lead 40b to and from the analyzer chip 20 are connected to a side of the planar plate 20b.

Figure 7A:
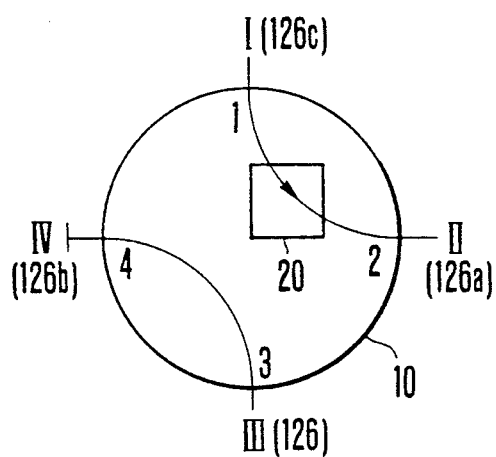
FIGS. 7A to 7F are schematic views showing a flow of the liquid in the embodiment shown in FIG. 1.

FIGS. 7A to 7F schematically show a flow of the carrier liquid and the sample to be analyzed in the embodiment shown in FIG. 1. In FIGS. 7A to 7F, the Roman numerals I to IV denote the numbers of the joints provided in the base 111 of the flow change-over valves and the like. In correspondence with the conceptional view shown in FIG. 9, the joint I is connected to the sample introduction pipe 126c, the joint II is connected the pipe 126a whose end is open, the joint III is connected to the separation carrier liquid introduction pipe 126, and the joint IV is closed or blocked as the pipe 126b. The Arabic numerals 1 to 4 denotes the holes formed in the upper surface of the upper plate 13 of the disc-like rotor assembly 10 shown in FIGS. 5 and 6. The holes 1 and 2 are communicated with the sample introduction section 22 of the chip 20 and the capillary 21a. FIG. 7A shows a condition where the sample introduction pipe 126c is communicated with the hole 1 and the open pipe 126a is connected to the hole 2. Under this condition, the sample 300 is injected from the sample introduction pipe 126c of the joint I at a pressure somewhat higher than the atmospheric pressure. The sample 300 is introduced through the hole 1 to fill the flow path or passage 14 within the disc-like rotor assembly 10 and the sample receiving region 22a within the chip 20 and to be discharged from the open pipe 126a of the joint II.

However, under this condition, since the sample 300 is kept under a relatively low pressure, the sample 300 cannot be introduced into the capillary 21a. In other words, in this stage, such a pressure is selected that the sample 300 is not introduced into the capillary groove 21a.

When the disc-like rotor assembly 10 is rotated through 90 degrees in the counterclockwise direction, the rotor 10 takes the position shown in FIG. B. When the rotor 10 is further rotated, the rotor 10 takes the position shown in FIG. 7C. In this case, the hole 1 of the disc-like body assembly 10 is connected to the carrier liquid introduction pipe 126 of the joint III, and the hole 2 is connected to the blocked portion 126b. Under this condition, when the carrier liquid 301 is introduced into the carrier liquid introduction pipe 26 of the joint III by applying a pressure for a short period of time, the sample filling the sample receiving region 22a within the chip 20 is partially introduced into the capillary 21a communicated with the sample receiving region 22a, since the hole 2 is blocked. Thereafter, the rotor 10 is further rotated counterclockwise through 90 degrees to take a position shown in FIG. 7D, so that the carrier liquid is fed through the carrier liquid introduction pipe 126 of the joint III. Thus, the sample remaining in the sample receiving region 22a and the flow path or passage 14 within the chip 20 is discharged through the hole 1 to the open pipe II.

Figure 7B:
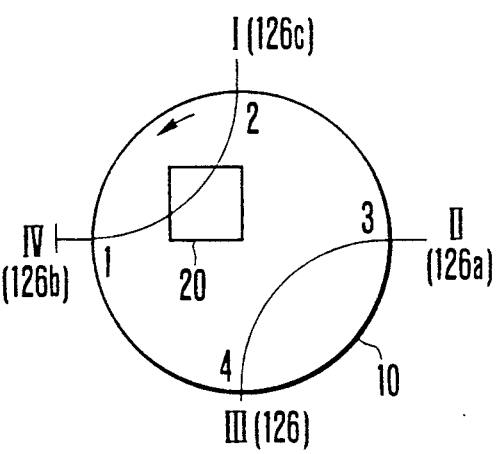
Figure 7C:
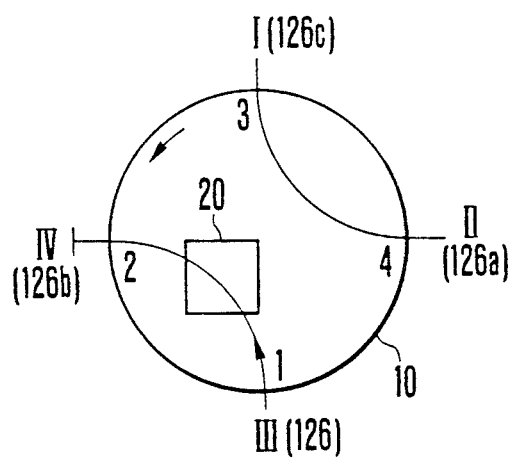
Figure 7D:
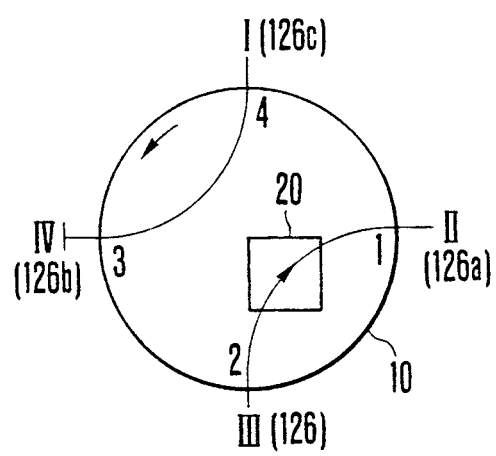

Incidentally, if desired, in the condition shown in FIG. 7B instead of the condition of FIG. 7C, a pulsative pressure may be applied to the sample introduction pipe 126c so that a part of the sample 300 within the sample receiving region 22a is fed into the capillary 21a.

Figure 7E:
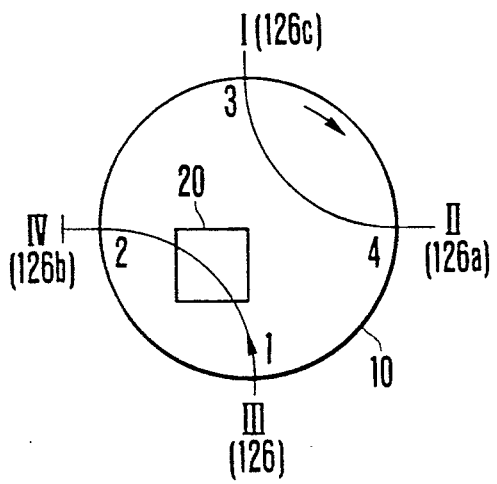

Subsequently, when the disc-like rotor assembly 10 is rotated clockwise through 90 degrees, the rotor 10 takes a position shown in FIG. 7E. This position is the same as that shown in FIG. 7C. When solution 301 is fed through the carrier liquid introduction pipe 126 of the joint III at a pressure greater than a pressure drop due to the flow resistance of the capillary 21a, the carrier liquid 301 is introduced into the capillary 21a through the sample receiving region 22a and is moved within the capillary 21a together with the sample 300 to be discharged from the downstream end of the capillary 21a through the detector 23. During a period of time flowing through the capillary 21a, each components or constituent in the sample 300 is separated. The separated components or constituents reach the detector 23 which in turn delivers signals in response to the concentrations of the respective constituents through the output lead 40b.

Figure 7F:
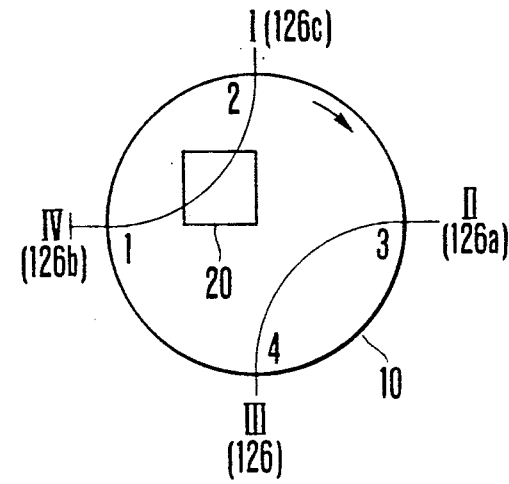

After the analysis, when the disc-like rotor assembly 10 is rotated clockwise through 180 degrees, the rotor 10 is returned to the initial stage shown in FIG. 7A through an intermediate stage shown in FIG. 7F. Thus, it is possible to analyze sample one after another by rotating the disc-like rotor assembly 10. The apparatus of this embodiment may be used in combination with the auto-sampler, a solenoid- or pneumatic flow-driven switching valve to provide a full automatic analyzer.

FIGS. 8A to 8D schematically show a sample introducing method to the separation column through a "pulsative pressure injection method" used in the embodiment of the invention. The "pulsative pressure injection method" means a method in which a high pressure Po is applied in a predetermined short period of time $t_0$ thereby injecting the liquid to the separating column.

Figure 8A:
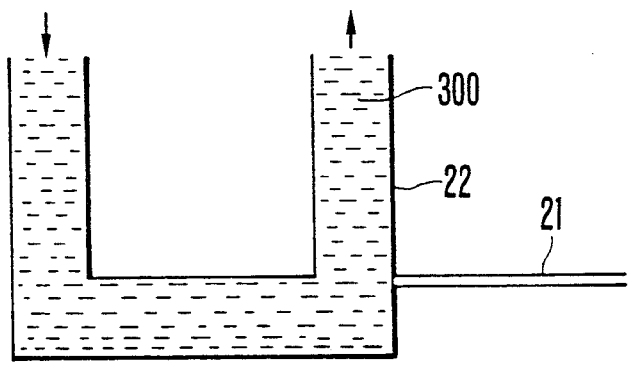
FIGS. 8A to 8D are schematic views showing a pulsative injection method according to an embodiment of the invention.
Figure 8B:
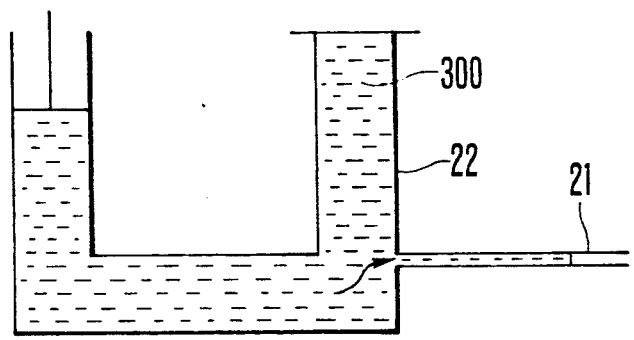
Figure 8C:
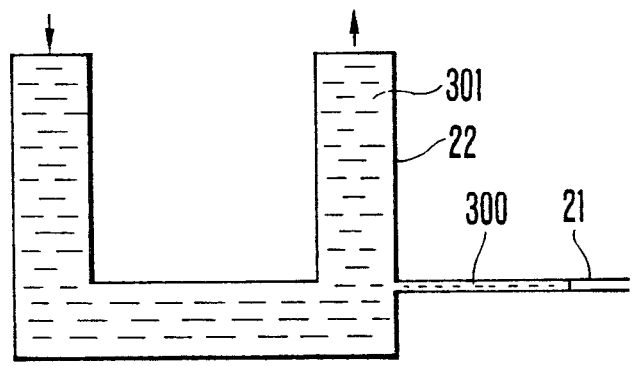
Figure 8D:
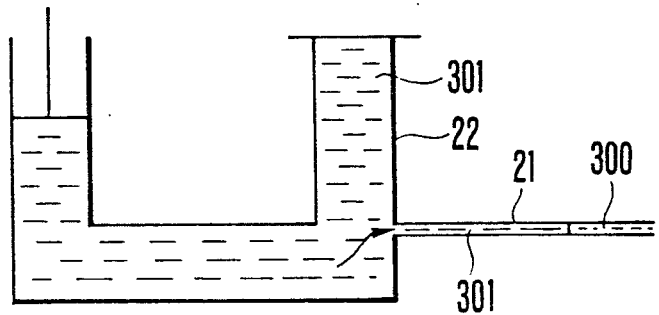

FIG. 8A shows a condition in which both ends of the sample introduction section 22 are released, and the sample 300 is injected into one end by using a syringe or the like to fill the section 22. Subsequently, when one end of the sample introduction section 22 is closed and the sample is pressurized at the other end for a short period of time t, a volume of the sample 300 proportional to a product of the pressure Po and the period of time $t_0$ is injected into the capillary 21a. FIG. 8B shows this condition. Subsequently, both ends of the sample introduction section 22 are opened as shown in FIG. 8C, and the carrier liquid 301 is injected into one end to thereby flow out the sample remaining in 5 the sample introduction section 22. At this time, a small volume of the sample 300 remains in the capillary 21a at a region close to an inlet thereof. Incidentally, instead of applying the pulsative pressure directly to the sample 300 as shown in FIG. 8B, it is possible to apply the pulsative pressure to the sample 300 in the sample introduction section 22 through the carrier liquid 301 as shown in FIG. 7C. Finally, as shown in FIG. 8D, one end of the sample introduction section 22 is closed and the carrier liquid 301 is pressurized from the other end. The carrier liquid 301 is introduced into the capillary 21a and is flown toward capillary 21a together with the sample an outlet of the 300.

Incidentally, instead of the disc-like rotor assembly, a rectangular disc 10 may be used to be reciprocatingly movable relative to the frame member. In this case, it is sufficient to provide, in the sliding surface of the rectangular assembly, openings which may be communicated with/blocked from the outer flow path.

In addition, it is possible to statically lay the assembly 10 in the frame member. In this case, since a satisfactory mechanical strength of the capillary 21a and the like is ensured by the assembly 10 per se or the combination of the assembly 10 with the frame member, it is possible to perform the piping connection with the outside parts with ease and without fail.

Another embodiment of the invention will now be described with reference to FIG. 10 which shows a disc-like rotor assembly 10 including an analyzer section. The other structure of the apparatus shown in FIG. 10 is the same as that of the first embodiment shown in FIG. 1, explanation of which will be omitted.

In FIG. 10, the analyzer section 20 is molded into molding material 41 such as ceramics or plastics and is built in the rotor 10. A flow path 14 for communication with a sample receiving region 22a of the chip 20 is formed. According to this embodiment, it is possible to manufacture the disc-like assembly 10 in the same manner as in the manufacturing process for the semiconductor elements or the like.

FIGS. 11 and 12 shows a disc-shaped rotor assembly 10 according to a third embodiment, the structure is the same as that of FIG. 1 except for the rotor 10. FIG. 11 is a longitudinal sectional view and FIG. 12 is a top plan view. Four communication holes 1 to 4 formed in the disc-like upper plate 13 are opened toward the circumferential wall of the disc-like upper plate 13. According to this embodiment, since the chip which is compact and fragile in a mechanical aspect is protected by the disc-like rigid members, it is easy to be handled in comparison with a conventional liquid chromatograph using a capillary made of thin glass tube.

Figure 13:
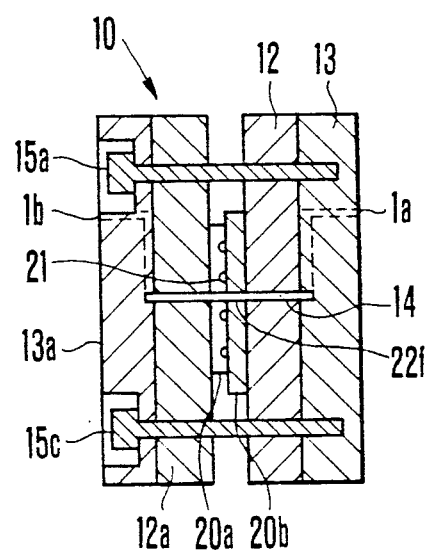
FIG. 13 is a cross-sectional view of a rotor according to a fourth embodiment of the invention.
Figure 14:
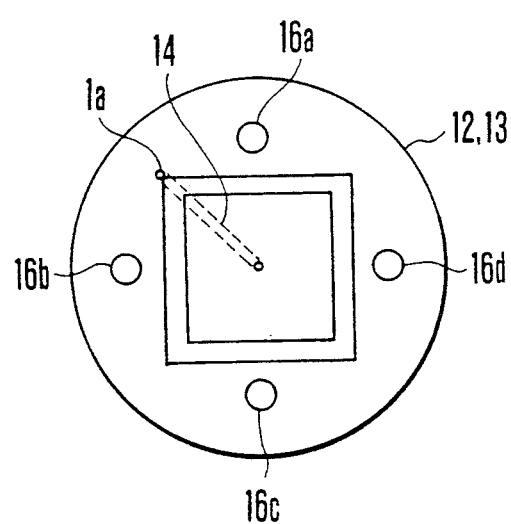
FIG. 14 is a plan view of the rotor shown in FIG. 13.

A fourth embodiment of the invention will now be described with reference to FIGS. 13, 14 and 15A to 5D. FIG. 13 is a sectional view showing a disc-like assembly 10 according this embodiment. FIG. 14 is a top plan view thereof. In FIG. 14, there is shown the rotor from which the upper plates 12a and 13a have been removed. In the disc-like assembly 10 according to this embodiment, a left half in FIG. 13 is symmetrical with a right half except for screw holes 16a to 16d. Communication holes 1a and 1b are opened through disc-like upper plates 12 and 12a. The flow path or passage 14 is connected in series with the passage in the sample introduction section 22f of the chip 20.

In this embodiment, only a pair of communication holes 1a and 1b are formed in the rotor 10.

FIGS. 15A to 15D schematically show a flow of the sample 300 and the carrier liquid 301 in the case where the disc-like rotor assembly 10 according to the embodiment shown in FIG. 13 is incorporated as a swiching valve. In FIGS. 15A to 15D, the Roman numerals I to IV denote the numbers of the joints provided on the base 111 such as the flow switching valves and the like. A sample introduction pipe 126c and a discharge pipe 126a are connected to the joints Ia and Ib, respectively, a carrier liquid introduction pipe 126 is connected to the joint IIa, and the joint IIb is closed or blocked as shown in the pipe 126b. A carrier liquid introduction pipe 126 and a carrier liquid discharge pipe 126a are connected to the joints IIIa and IIIb respectively, the carrier liquid introduction pipe 126 is connected to the joint IVa and the joint IVb is closed as in the pipe 126b.

Figure 15A:
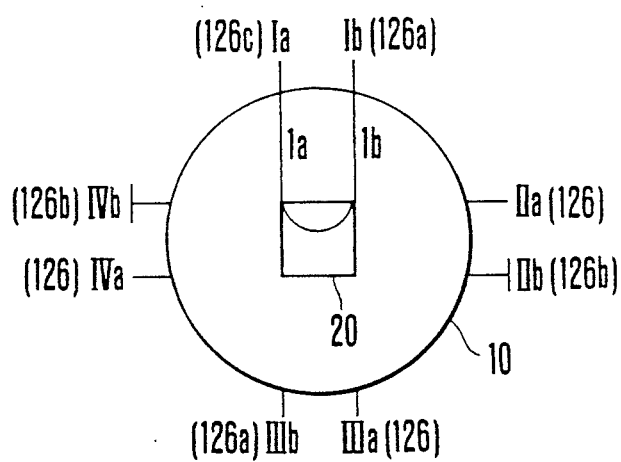
FIGS. 15A to 15D are schematic views showing a flow of liquid in the fourth embodiment.
Figure 15B:
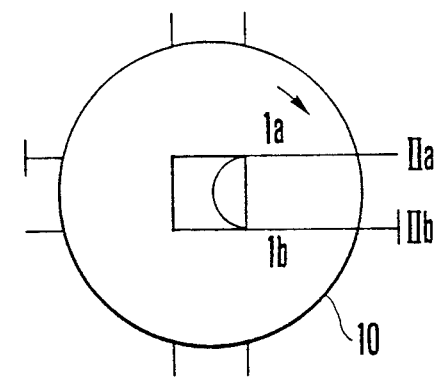

First of all, under the condition shown in FIG. 15A, the sample 300 is introduced from the sample introduction pipe Ia at a pressure somewhat higher than the atmospheric pressure to fill the sample injection section 22f within the chip 20 and the flow path 14 and is then sealed. At this time, the sample 300 is not introduced into the capillary 21a due to the high flow resistance of the capillary 21a. Thereafter, the disc-like assembly 10 is rotated clockwise through 90 degrees to take the position shown in FIG. 15B. A hole 1a of the disc-like assembly 10 is connected to the carrier liquid introduction pipe IIa and a hole 1b is closed. Under this condition, when the carrier solution is fed for a short period of time at a high pressure, the sample is partially introduced into the capillary 21b in communication with the sample introduction section 22f.

Figure 15C:
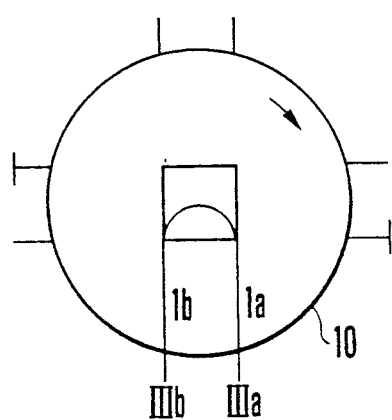
Figure 15D:
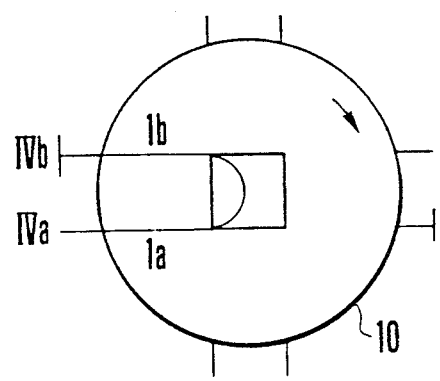

Subsequently, the disc-like assembly 10 is further rotated clockwise through 90 degrees to take the position shown in FIG. 15C. Under this condition, since the holes 1a and 1b are connected to the carrier liquid introduction pipe and the discharge pipes IIIa and IIIb, the carrier liquid is fed to flow out the sample residing in the flow path or passage 14 and the sample introduction section 22f. Further, the disc-like assembly 10 is rotated through 90 degrees to take the position shown in FIG. 15D. At this time, the hole 1a is connected to the carrier liquid introduction pipe IVa and the hole 1b is closed. In this case, when the carrier liquid is fed at the pressure higher than the flow resistance of the capillary 21a, the carrier liquid is introduced into the capillary 21a through the sample introduction section 22. The sample is flown within the capillary 21a to be separated and detected, i.e. to be analyzed. Thus, according to the embodiment shown in FIG. 13, since the holes required for introduction of the liquid to the disc-like assembly may be only the two holes 1a and 1b, the structure can be much simplified.

FIG. 16 shows a structural example where processing from the introduction of the sample to the measurement thereof is automatically performed. An analyzer body 30 of the flow switching valve type into which the analyzer chip 20 is incorporated is fixed to a housing 45 incorporating therein a motor 31 and a board having a circuit (not shown) for controlling operation of the motor 31. A shaft 117 of the analyzer body 30 is coupled to a shaft 32 of the motor 31. Since the rotational direction and rotational angle of the motor 31 is controlled by the circuit (not shown), it is possible to automate the operation by the combination with the auto-sampler.

According to the foregoing embodiment, it is possible to miniaturize the analytical section and to realize a liquid chromatograph which is easy to handle.

FIG. 17 is a cross-sectional view of a sample introduction device 18 in accordance with another embodiment of the invention. In substrate 20a made of silicon or glass, there are formed grooves 21 for a capillary 21a having an inner diameter of 0.5 to 50 micrometers, preferably, 1.5 to 5 micrometers, a part of the sample introduction flow path or passage 22 having an inner diameter ten times or more greater than that of the capillary 21a, preferably 50 to 300 times greater than that of the capillary 21a, and a communication portion between the capillary 21a and a sample receiving region 22a of the sample introduction flow path or passage 22. In a substrate 20b made of silicon or glass, which has through-holes 22g for sample introduction and a hole 8 for receiving a pipe 24 for communication with the sources of the separation carrier liquid and the sample. The plate 20b and the substrate 20a are bonded to each other to form the respective flow paths. Although it is preferable that the inner diameter of the sample introduction flow path 22 be much larger than that of the capillary 21a, the inner diameter of the sample introduction flow path will be limited by the amount of sample available. Thereafter, the pipe 24 is inserted into the hole 8 and fixed thereto by adhesives 25 such as epoxy resin or the like. One of the pipes 24 is connected to a valve 50b for opening/closing the passage in the pipe 24, whereas the other is connected to the flow path or passage from the sources of the carrier 301 and the sample 300 through a switching valve 50a. The grooves 21 in the silicon or glass substrate 20a are formed by lithography and etching techniques generally used in the manufacturing process of semiconductor integrated circuits. As shown in FIG. 2, the capillary grooves 21 of the capillary 21a are in the form of a spiral shape in order to make its length long. The starting point of the capillary groove 21 and the sample introduction flow path 22 have the communication part 5 at the central part of the sample receiving portion 22a. A detector or detecting part 23 such as an electrical conductivity meter is provided at the downstream end of the capillary groove 21.

Figure 18:
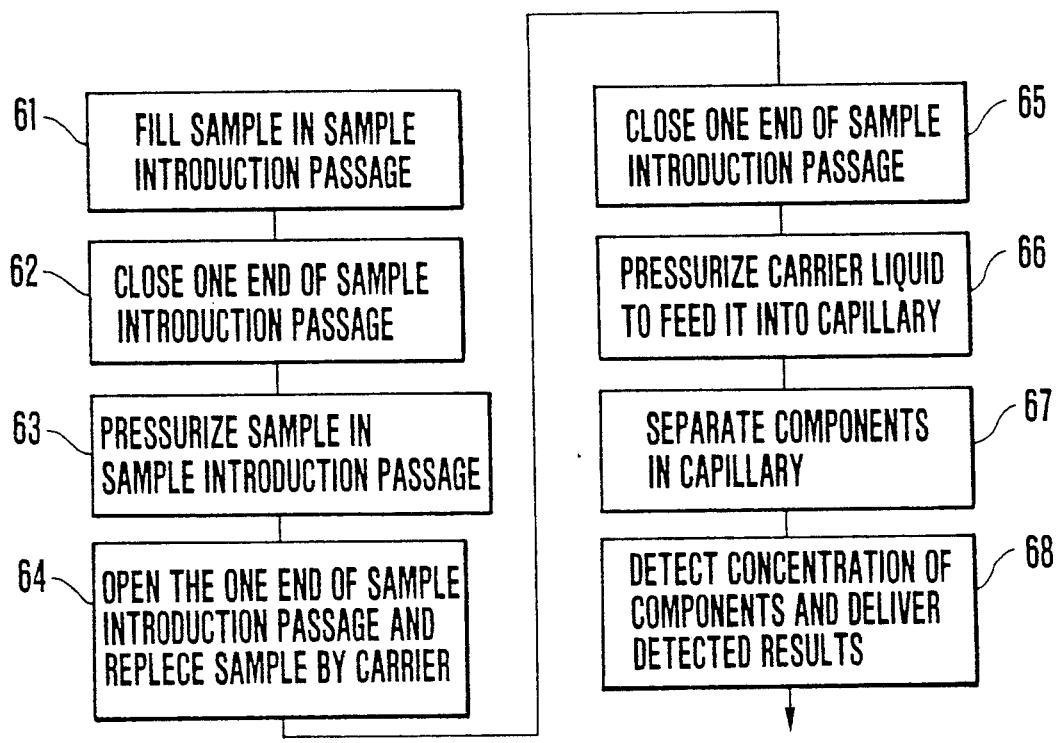
FIG. 18 is a flowchart or flow-sheet showing operation of the liquid chromatograph according to an embodiment of the invention.

FIG. 18 is a flowchart showing in more detail an operation of the liquid chromatograph using a sample introducing method which is substantially the same as that described in conjunction with FIGS. 7A to 7F. First of all, the valve 50b is opened and one end of the sample introduction flow path or passage 22 is released to fill the sample 300 in the flow path 22 (step 61). Subsequently, the valve 50b is closed, thereby one end of the flow path 22 being closed (step 62). The sample 300 in the flow path 22 is pressurized for a short period of time (step 63). In this case, by increasing/decreasing the pressurizing period $t_0$ and the pressure Po, the amount of the sample to be introduced into the capillary 21a is controlled. After the completion of the pressurizing of the sample 300 in the flow path 22, both ends of the sample introduction flow path 22 are opened by the valves 50a and 50b, so that the sample 300 in the flow path 22 is replaced by the carrier liquid 301 in step 64. Thereafter, in step 65, one end of the flow path 22 is closed by the valve 50b to pressurize and feed the carrier liquid 301. Subsequently, in step 66, the pressure of the carrier liquid 301 is made higher than the flow resistance of the capillary 21a, and the carrier liquid 301 is fed into the capillary 21a to flow with the sample 300. Furthermore, in step 67, the respective constituents or components of the sample 300 are separated while flowing through the capillary 21a. In step 68, the constituents or components are detected by the detector or detecting part 23 disposed in the downstream end of the capillary 21a.

Figure 19:
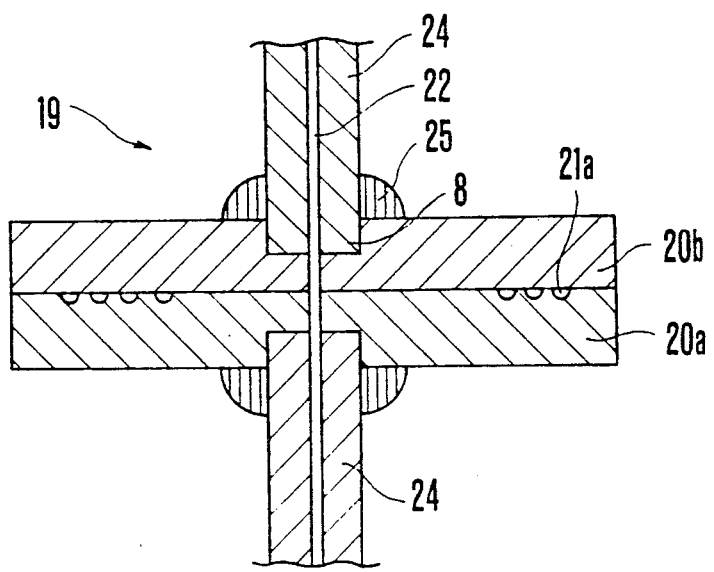
FIG. 19 is a sectional view showing still another embodiment of the invention.

FIG. 19 is a cross-sectional view showing a sample introduction device 19 for a liquid chromatograph according to still another embodiment of the invention. Pipes 24 for introducing/discharging the sample 300 and the separation carrier liquid 301 are arranged in confronted relation with base plates 20b, 20a made of silicon or glass. The sample introduction flow path or passage 22 is vertically arranged through the surfaces of the base plates 20a, 20b. The other structure is the same as that of the embodiment shown in FIG. 17.

Figure 20:
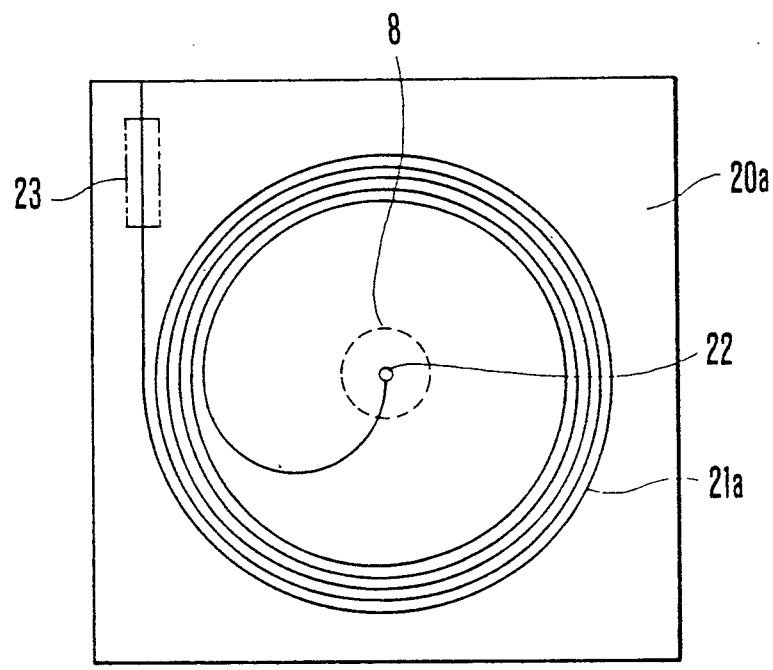
FIG. 20 is a plan view of the embodiment of FIG. 19.

FIG. 20 is a plan view of the embodiment shown in FIG. 19 from which the silicon or glass base plate 20b has been removed. The sample introduction flow path is opened through the base plate 20a. A hole 8 for mounting the end of the pipe 24 is opened in the rear side. The other structure is the same as that shown in FIG. 2. The operation of the liquid chromatograph shown in the embodiment of FIG. 19 is represented by the flowchart shown in FIG. 18 in the same manner as in the embodiment shown in FIG. 17.

Figure 21:
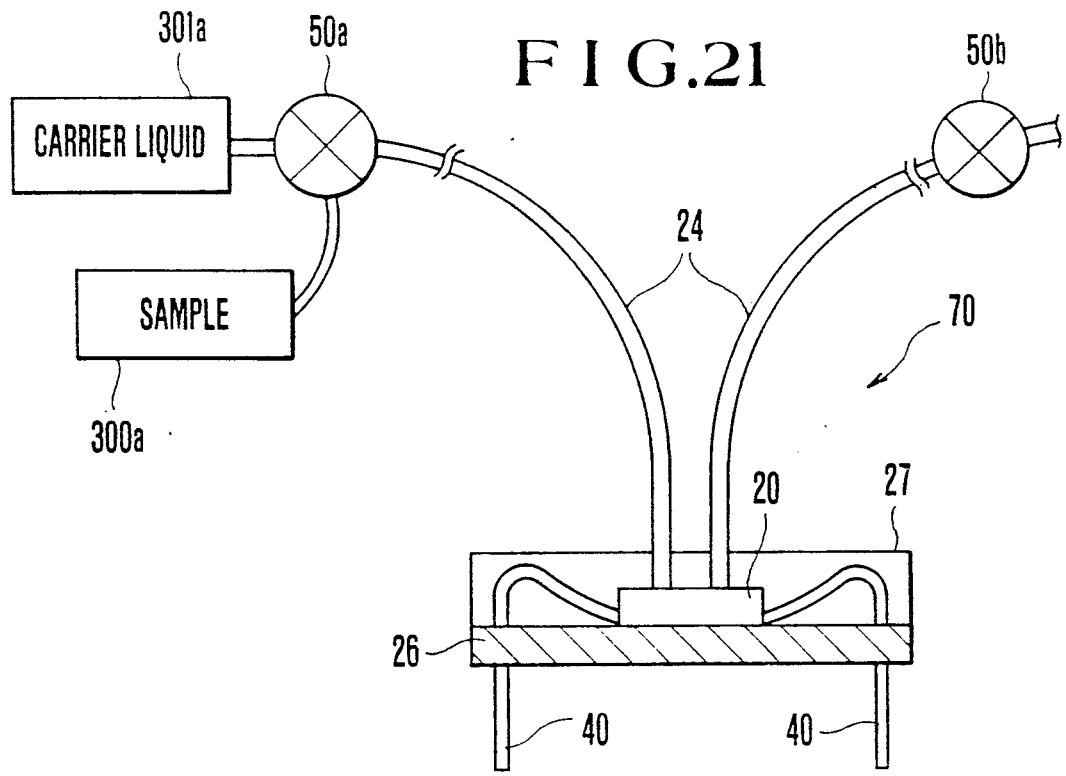
FIG. 21 is a sectional view showing the overall structure according to still another embodiment of the invention.

FIG. 21 is a cross-sectional view of the overall structure of the liquid chromatograph 70 in accordance with an embodiment in case of an example shown in FIG. 17. In this case, the chip 20 is statically disposed and the opening/closing of the flow path 22 is performed by the external valves 50a and 50b. The silicon or glass substrate 20 having a capillary therein is fixed onto a mount 26. The substrate 20 is covered by a cover 27, and the pipes 24 for connection to the sample 300 and the carrier liquid 301 are mounted on an upper surface of the substrate 20 to pass through the cover 27. The pipe 24 is connected to the sample or separation carrier liquid sources 300a, 301a through the flow path switching valve 50a. The power supply to the detector 23 and the transfer of the output signal therefrom are carried out through leads 40a and 40b.

EXAMPLE 1

An inner diameter of the sample introduction passage 22 was 250 micrometers. An inner diameter dc of the capillary 21a was 4 micrometers and its length Lc was 18 cm. The liquid sample was prepared by dissolving an original sample in a liquid (water) having a viscosity of 0.001 Ns/m². The separation was carried out by the capillary liquid chromatograph provided with the sample introduction device 18 in accordance with the embodiment shown in FIG. 17. In this example 1, it was preferred that the injected amount of sample 300 should be less than 4.9 picoliters, and the flow rate of the carrier liquid 301 should be as high as 4.2 nanoliters/min (at this time, the pressure Po was about 20 kg/cm²). Under this condition, the electrolytes such as Na+ were separated. The carrier liquid 301 was adjusted to meet the equation k′=1, where k′ means a capacity defined by k′

$$= \frac{t_R - t_1}{t_1}.$$

Figure 22:
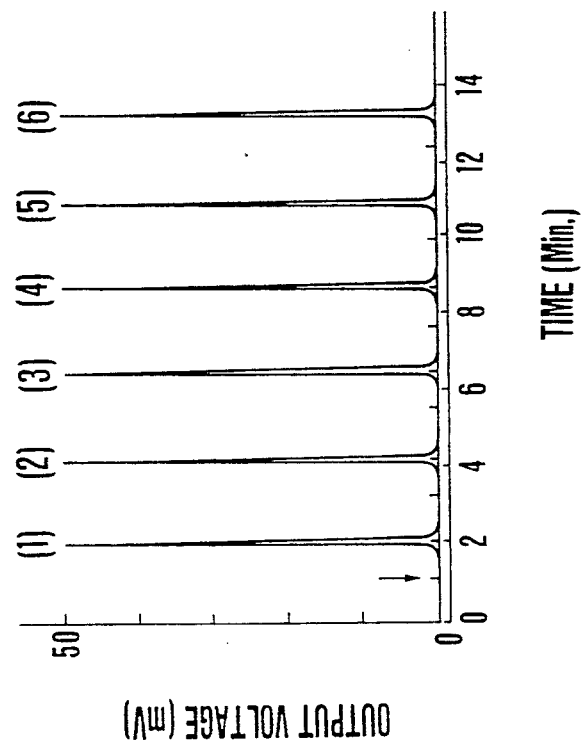
FIG. 22 is a graph showing reproducibility of the device according to one embodiment of the invention.

$t_1$ being a hold-up time and $t_R$ being a retention time. The hold-up time $t_1$ was determined by [(void volume in the separation column)+(volume in passages)+(volume in the cell)]/(flow rate). A height to a theoretical plate was 3.2 micrometers. Also, the retention time was 64 seconds. FIG. 22 shows a reproducibility of peak heights obtained in the Example 1. The pressurizing period $t_0$ of the sample was 2.8 seconds, and the pressure Po was about 20 kg/cm². An electric conductivity detector having a capacity of 2.9 picoliters was used as the detecting part 23. As is apparent from FIG. 22, it is understood that sufficient reproducibility is ensured by the sample introduction device 18 and the method of the liquid chromatograph in accordance with the embodiment of the invention. Incidentally, the normal low molecular components have a diffusion coefficient $D = 1.6 \times 10^2$ m²/s. A maximum period during which the injected amount was not affected even if the sample 300 was left in the sample introduction flow path 22 was 16 seconds.

According to the present invention, in the sample introduction section of the liquid chromatograph using the capillary as the separating column, an inner diameter of the sample introduction flow passage is increased, and it is possible to perform the introduction and the numerical analysis of the sample only by the pressurizing operation of the liquid. Therefore, the structure for the liquid chromatograph is simplified and the manufacturing process may be facilitated.

A preferred embodiment of a detector 23 for the liquid chromatographs shown in FIGS. 2 and 20 will now be described with reference to FIGS. 23 and 24.

Figure 23:
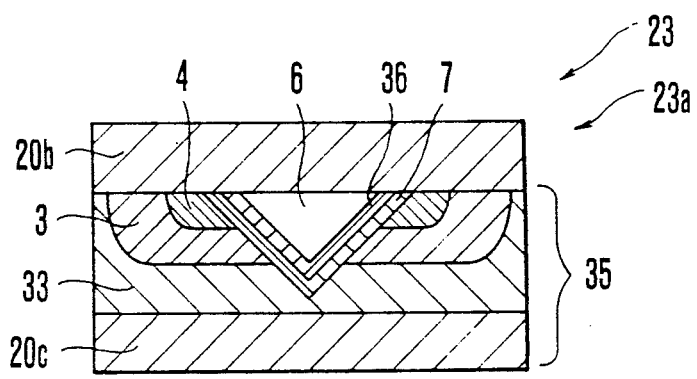
FIG. 23 is a cross-sectional view showing one example of a chromatographic detector or detecting part according to the invention.

In FIG. 23, on a silicon substrate 20c doped at a high concentration, there is formed an epitaxial layer 33 doped at a low concentration in the same conductivity type as that of the substrate 20c. The substrate 20c and the epitaxial layer 33 serve as a source of an FET. A well layer 3 having a conductivity type opposite to that of the substrate 20c and the epitaxial layer 33 is provided in the epitaxial layer 33. A drain layer 4 having the same conductivity type as that of the substrate 20c and the epitaxial layer 33 is formed in the well 3. On a surface of the drain 4 of the thus formed wafer 35, there is formed a groove portion 6 by etching. A gate insulative layer 7 and an ion-sensitive layer 36 are formed in order on side walls of the groove portion 6. In addition, on the surface of the wafer 35 provided with the groove portion 6, there is bonded a seal plate 20b formed of, for example, borosilicate glass (corresponding to "Pyrex", resistered trademark) for sealing the opening portion of the groove portion 6 to define the flow passage for the liquid sample. The groove portion 6 reaches the epitaxial layer 33 in a depth direction. The part of the well 3 in contact with the gate insulative membrane 7 serves as a channel of the FET. Therefore, in order to exhibit a desired electric property for the FET, it is necessary to keep a distance between the drain 4 and the epitaxial layer 33 at an appropriate level in the range of 1 micrometer to 100 micrometers with a high precision.

An experimental example for evaluation of the property of the detector 23 according to this embodiment will now be described.

EXAMPLE 2

An N-type silicon plate having a resistivity of 0.01 Ω.cm was used as the substrate 20c on which an epitaxial layer 33 made of N-type silicon with a resistivity of 10 Ω.cm was formed to have a thickness of 10 microns. The well 3 made of P-type silicon was formed to have a thickness of 5 microns in the epitaxial layer 33. A drain 4 having a thickness of one micrometer was formed in the well 3. A groove portion 6 having a depth of 7 micrometers was formed on an upper surface of the thus formed wafer 35. A gate insulative layer 7 formed on the side walls of the groove portion 6 was of the double structure of $SiO_2$ having a thickness of 500 Å and $Si_3N_4$ having a thickness of 1000 Å. The ion sensitive layer 36 deposited on the gate insulative layer 7 was made from polyvinyl chloride (PVC) as a base material into which plasticizer of tetra-undecyl 3, 3', 4, 4'-benzohydro-tetracarboxylate (BTCU) and an ion selective substance of 12-crown-4 of crown compounds were added. The membrane 36 functioned as a positive ion sensitive membrane. Also, the thickness of the Pyrex glass forming the seal plate 20b was 0.5 mm.

Figure 24:
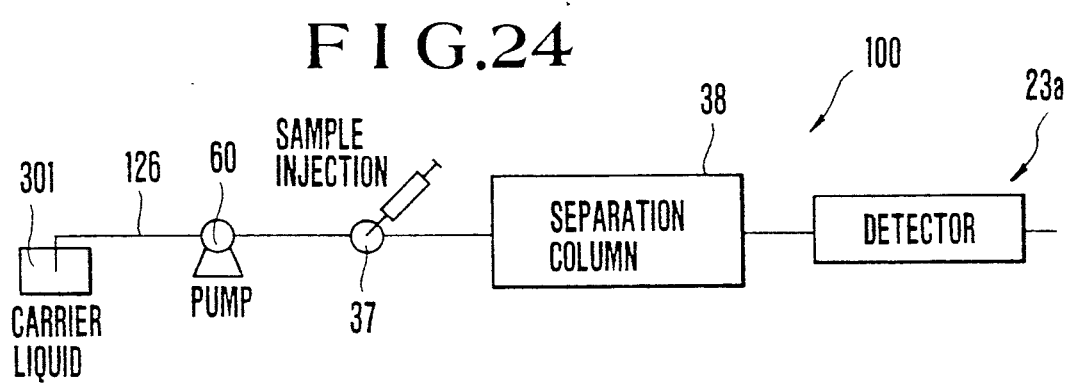
FIG. 24 is a view showing the chromatographic system using the detector shown in FIG. 23.
Figure 25:
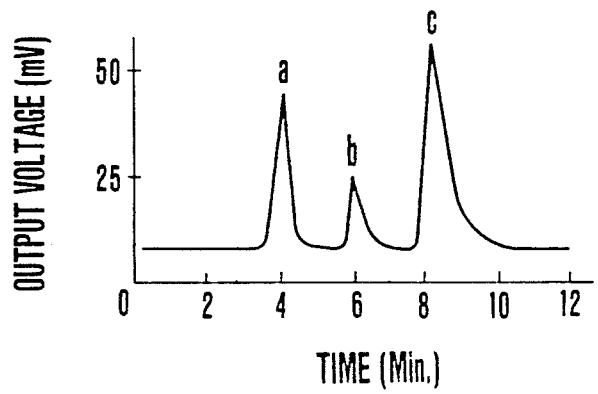
FIG. 25 is a graph showing the experimental results in the example shown in FIG. 24.

The thus formed FET detector 23a was incorporated into the liquid chromatograph system 100 shown in FIG. 24. In FIG. 24, the carrier liquid 301 was fed through the tube 126, the sample injection system 37 and the separation column 38 into the FET detector 23a by the pump 60. $HNO_3$ solution of 2 mM was used as the carrier liquid 301, and a positive ion exchange column filled with minute particles in which sulfo group was introduced onto surfaces of stylenebenzene copolymer was used as the separating column 38. FIG. 25 shows a chromatogram in which a liquid mixture containing $10^{-3}$M of $Na^+$, $K^+$ and $NH_4^+$ ions was introduced, into the liquid chromatograph system 100, as the liquid sample. In FIG. 25, the peaks a, b and c correspond $Na^+$, $NH_4^+$ and $K^+$ ions, respectively.

According to the Example 2 above, by integrally incorporating the FET detector 23a onto the substrate 20c, it is possible to provide a compact, inexpensive detector 23a of the ions separated in the separation column 38 of the liquid chromatograph system 100.

More preferably, as shown in FIG. 2 or FIG. 20, the FET detector 23a and the column 21a are integrally formed in a single chip 20, whereby a connection part between the detector 23a and the column 21a is shortened as small as possible, thereby reducing the peak-broadening of the detection output or the broadening of the concentration distribution of the sample in the carrier due to the existence of the connection part. In this case, the wafer 35 shown in FIG. 23 corresponds to the substrate 20a shown in FIG. 2 or FIG. 20.

Figure 26:
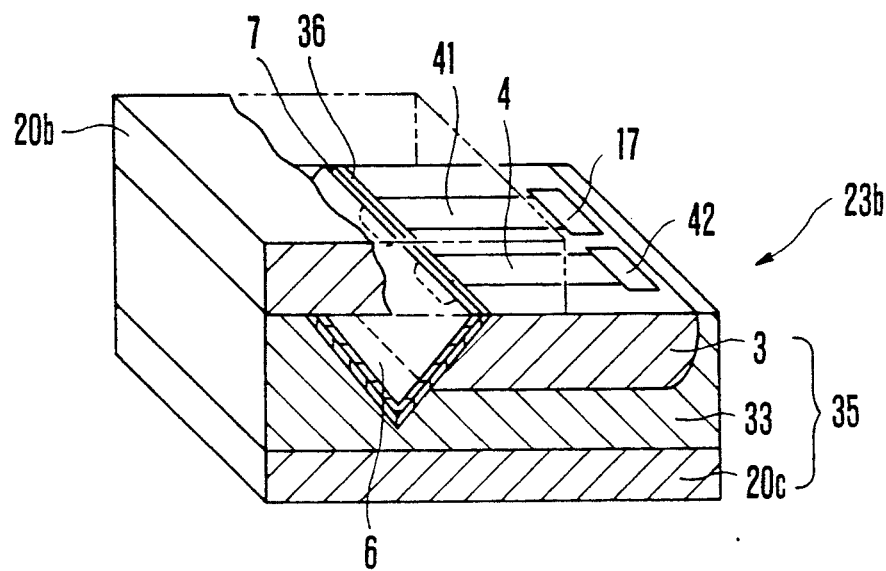
FIGS. 26 to 28 are a perspective view, a cross-sectional view and a perspective view of the detectors according to the respective modifications.
Figure 27:
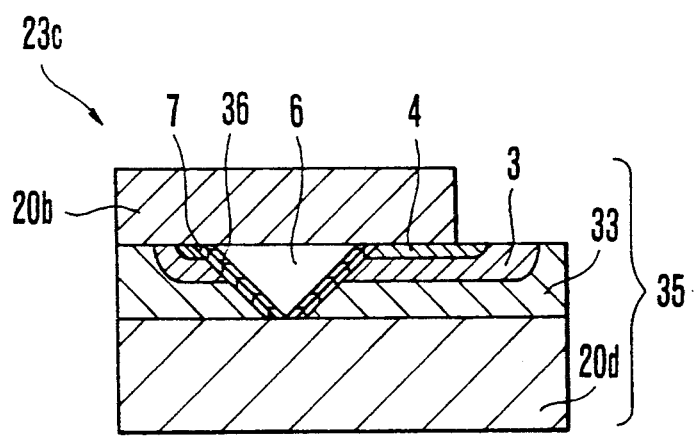
Figure 28:
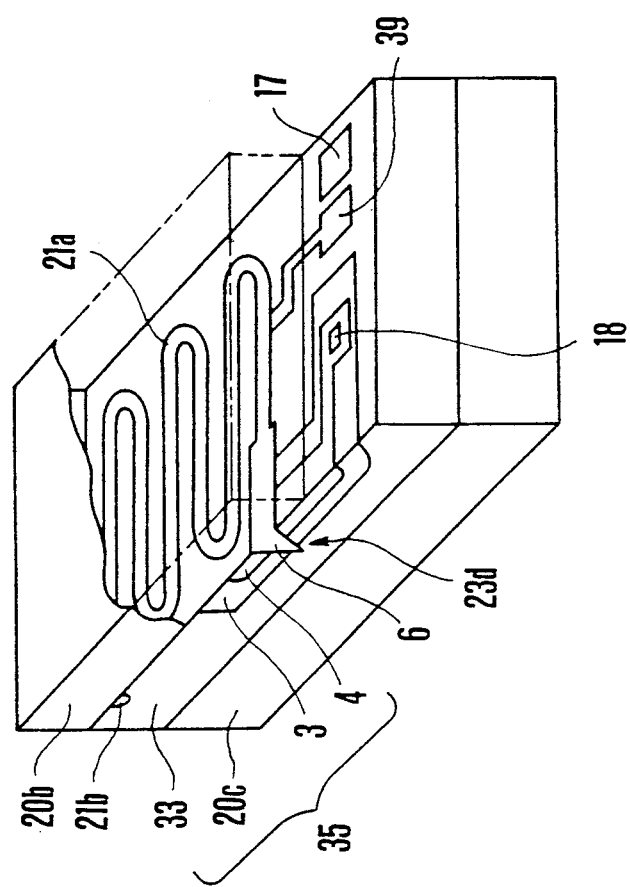

FIGS. 26, 27 and 28 show first, second and third modifications of the FET detector, respectively. In these figures, the same reference numerals or characters are used to indicate the same or similar elements or components as in the FET detector 23a shown in FIG. 23 and explanation therefor will be omitted. In the first modification shown in FIG. 26, a source 41 and a drain 4 of the FET are formed in the common surface of the wafer 35. According to this modification, when a source electrode 17 and a drain electrode 42 are connected to external circuits, respectively, leads therefor may be provided from the same surface, thereby facilitating the lead wire connection work.

In the detector 23c of the second modification shown in FIG. 27, the substrate 20c is formed of sapphire 20d. According to this modification, when the substrate 20d is not etched. Therefore, it is possible to control the depth of the groove portion 6 in accordance with the thickness of the epitaxial layer 33 to thereby form the groove portion 6 with high precision.

In the detector 23d of the third modification shown in FIG. 28, the detector 23d and the capillary separation column 21a are formed integrally on the same substrate 20c. Although, in this example, the column 21a is surpentine, the column 21a may be spiral as shown in FIG. 2. The column 21a is defined by a capillary groove 21 formed in Si substrate by etching and the Pyrex glass plate 20b. A layer made of $SiO_2$ or a double structure membrane made by combination of $SiO_2$ with $Si_3N_4$, $Al_2O_3$, $Ta_2O_5$ or $ZrO_2$ and the like is formed on the surface of the groove 21. The membrane or layer corresponds to the layer 210 shown in FIG. 3, and may serve as the gate insulative layer 7. At one end of the column 21a, there is formed a detector or detecting part 23d that is substantially the same as the detector 23a shown in FIG. 23. The other end serves as a column inlet 21b through which the sample is introduced. Reference numeral 39 denotes a reference electrode for applying a bias voltage to the gate. According to this modification, the FET detector 23d and the column 21a are formed integrally with each other to thereby make the liquid chromatograph system compact.

As described above, according to the present invention, a detector having an FET transistor type chemical sensor in the liquid chromatograph is formed integrally with the substrate. Therefore, it is possible to provide a compact and inexpensive detector for a liquid chromatograph which may detect the constituent ions contained in the liquid sample.

What is claimed is:

1. A liquid chromatograph comprising:
    an analyzing chip for analyzing a liquid sample, said analyzing chip including a substrate having a capillary groove formed therein, detecting means disposed downstream of said capillary groove, and a cover covering said capillary groove, thereby forming a capillary having an inlet and an outlet;
    a frame member constituting an outer valve member and having formed therein a liquid sample introduction path, a carrier liquid introduction path, and a liquid discharge path; and
    a rigid member in which said analyzing chip is mounted, said rigid member constituting an inner valve member and being movably disposed within said frame member to enable said inlet and said outlet of said capillary to be selectively connected to and disconnected from said liquid sample introduction path, said carrier liquid introduction path, and said liquid discharge path when said rigid member is moved relative to said frame member.

2. A liquid chromatograph according to claim 1, wherein the capillary groove has an inner diameter of 0.5 to 50 micrometers, and the liquid sample introduction path has an inner diameter 10 or more times larger than the inner diameter of the capillary groove.

3. A liquid chromatograph according to claim 3, wherein the detecting means is an FET-type chemical sensor for detecting component ions contained in the liquid sample, and wherein a wall surface of a part of the capillary groove serves as a gate insulative membrane of the FET-type chemical sensor.

4. A liquid chromatograph comprising:
an analyzing chip for analyzing a liquid sample, said analyzing chip including a substrate having a capillary groove formed therein for conveying a carrier liquid, detecting means connected to said capillary groove, and a cover covering said capillary groove to form a capillary;
a frame member within which said analyzing chip is disposed; and
carrier liquid feeding means disposed outside said frame member for feeding said carrier liquid into said capillary;
wherein said analyzing chip is clamped between disc-shaped rigid members to form a rotor, said rotor being rotatably disposed within said frame member to enable flow paths in said liquid chromatograph to be changed by rotating said rotor.

5. The liquid chromatograph according to claim 2, wherein said capillary groove is subjected to a surface treatment suitable for enabling separation of components of said liquid sample after said capillary groove is formed in said substrate.

6. The liquid chromatograph according to claim 2, wherein said detecting means comprises detection terminals of an electrochemical detector or an electrical conductivity detector.

7. A liquid chromatograph comprising:
a frame member having an inner space and being provided with a liquid sample introduction hole for conveying a liquid sample to be analyzed by liquid chromatography from outside the frame member to the inner space, a carrier liquid introduction hole for conveying a carrier liquid from outside the frame member to the inner space, and a liquid discharge hole for conveying the liquid sample and the carrier liquid from the inner space to outside the frame member; and
a rotor valve body disposed within the inner space of the frame member so as to be rotatable relative to the frame member and to form a liquid-tight seal with at least one surface of the inner space of the frame member, the rotor valve body having mounted therein an analyzing chip for analyzing the liquid sample by liquid chromatography;
the analyzing chip comprising:
a substrate having a principal surface and a capillary groove formed in the principal surface;
a cover plate sealed to the principal surface of the substrate to form a liquid-tight seal with the principal surface of the substrate and to establish a capillary column for liquid chromatography in cooperation with the capillary groove; and
detecting means connected to a downstream end of the capillary column for detecting components of the liquid sample in the form of a liquid chromatogram;
wherein the rotor valve body has an outer surface provided with first, second, third, and fourth holes, the first and second holes being connected with the capillary column and the third and fourth holes being connected with each other, and wherein the rotor valve body is rotatable to a plurality of rotational positions to selectively connect three holes selected from the first, second, third, and fourth holes with the liquid sample introduction hole, the carrier liquid introduction hole, and the liquid discharge hole in the frame member.

* * * * *